United States Patent
Harada et al.

(10) Patent No.: US 11,149,045 B2
(45) Date of Patent: Oct. 19, 2021

(54) RAW MATERIAL FOR VAPOR DEPOSITION INCLUDING ORGANOPLATINUM COMPOUND AND VAPOR DEPOSITION METHOD USING THE RAW MATERIAL FOR VAPOR DEPOSITION

(71) Applicant: TANAKA KIKINZOKU KOGYO K.K., Tokyo (JP)

(72) Inventors: Ryosuke Harada, Tsukuba (JP); Shigeyuki Ootake, Tsukuba (JP); Toshiyuki Shigetomi, Tsukuba (JP); Kazuharu Suzuki, Tsukuba (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 135 days.

(21) Appl. No.: 16/628,195

(22) PCT Filed: Jul. 12, 2018

(86) PCT No.: PCT/JP2018/026261
§ 371 (c)(1),
(2) Date: Jan. 2, 2020

(87) PCT Pub. No.: WO2019/021836
PCT Pub. Date: Jan. 31, 2019

(65) Prior Publication Data
US 2020/0148713 A1    May 14, 2020

(30) Foreign Application Priority Data
Jul. 25, 2017  (JP) .............................. JP2017-143327

(51) Int. Cl.
*H01L 21/285* (2006.01)
*C07F 15/00* (2006.01)
(Continued)

(52) U.S. Cl.
CPC .......... *C07F 15/0086* (2013.01); *C23C 16/18* (2013.01); *H01L 21/28518* (2013.01); *H01L 29/45* (2013.01)

(58) Field of Classification Search
CPC ..... C07F 15/0086; C23C 16/18; H01L 21/28; H01L 21/28518; H01L 21/28556; H01L 29/45
See application file for complete search history.

(56) References Cited

U.S. PATENT DOCUMENTS 5,783,716 A    7/1998  Baum et al.
5,929,267 A *  7/1999  Kadokura ............... C23C 16/18
                                                      556/136
(Continued)

FOREIGN PATENT DOCUMENTS

JP    H11-292889 A    10/1999
JP    2001-504159 A    3/2001
(Continued)

OTHER PUBLICATIONS

International Searching Authority, "International Search Report," issued in connection with International Patent Application No. PCT/JP2018/026261, dated Sep. 11, 2018.
(Continued)

*Primary Examiner* — Jaehwan Oh
(74) *Attorney, Agent, or Firm* — Foley & Lardner LLP (57) ABSTRACT

A raw material for vapor deposition for producing a platinum thin film or a platinum compound thin film by a vapor deposition method. The raw material for vapor deposition includes an organoplatinum compound represented by the following formula, in which a cyclopentene-amine ligand and an alkyl ligand are coordinated to divalent platinum. The organoplatinum compound of the present invention has
(Continued)

moderate thermal stability and can respond flexibly to severe film formation conditions, including a wider film formation area, higher throughput, and the like.

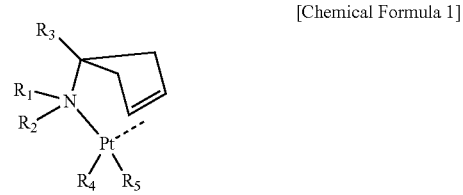

[Chemical Formula 1]

(In the formula, $R_1$, $R_2$, and $R_3$ are each any one of a hydrogen atom, an alkyl group, an alkenyl group, an alkynyl group, an amino group, an imino group, a cyano group, and an isocyano group, each having 4 or less carbon atoms, and $R_4$ and $R_5$ are each an alkyl group having 1 or more and 3 or less carbon atoms.)

11 Claims, 2 Drawing Sheets

(51) Int. Cl.
*C23C 16/18* (2006.01)
*H01L 29/45* (2006.01)

(56) References Cited

U.S. PATENT DOCUMENTS

| | | | | |
|---|---|---|---|---|
| 6,162,712 | A | * 12/2000 | Baum | C07C 49/92 438/580 |
| 8,911,827 | B2 | * 12/2014 | Suzuki | C23C 16/18 427/250 |
| 2010/0119406 | A1 | * 5/2010 | Dussarrat | C07F 15/006 420/463 |
| 2015/0030772 | A1 | * 1/2015 | Saito | C23C 16/18 427/252 |
| 2018/0066357 | A1 | * 3/2018 | Harada | C23C 16/46 |

FOREIGN PATENT DOCUMENTS

| JP | 2016-211048 A | 12/2016 |
|---|---|---|
| WO | WO-2010/052672 A2 | 5/2010 |
| WO | WO-2012/144455 A1 | 10/2012 |
| WO | WO-2013/054863 A1 | 4/2013 |

OTHER PUBLICATIONS

International Searching Authority, "Written Opinion," issued in connection with International Patent Application No. PCT/JP2018/026261, dated Sep. 11, 2018.

* cited by examiner

SiO$_2$ SUBSTRATE

Si SUBSTRATE

RAW MATERIAL FOR VAPOR DEPOSITION INCLUDING ORGANOPLATINUM COMPOUND AND VAPOR DEPOSITION METHOD USING THE RAW MATERIAL FOR VAPOR DEPOSITION

CROSS-REFERENCE TO RELATED APPLICATIONS

The present application claims priority under 37 U.S.C. § 371 to International Patent Application No. PCT/JP2018/026261, filed Jul. 12, 2018, which claims priority to and the benefit of Japanese Patent Application No. 2017-143327, filed on Jul. 25, 2017. The contents of these applications are hereby incorporated by reference in their entireties.

TECHNICAL FIELD

The present invention relates to a raw material for vapor deposition including an organoplatinum compound, for producing a platinum thin film or a platinum compound thin film by a vapor deposition method such as a CVD (chemical vapor deposition) method or an ALD (atomic layer deposition) method. Specifically, it relates to a raw material for vapor deposition, which enables film formation at a low temperature and yet has moderate thermal stability, and is capable of efficiently forming a platinum thin film, etc.

BACKGROUND ART

As electrode/wiring materials for various semiconductor elements and semiconductor devices, platinum thin films and platinum compound thin films (hereinafter referred to as "platinum thin film, etc.") have been conventionally applied. Then, in the production of a platinum thin film, etc., a vapor deposition method such as a CVD method or an ALD method has been utilized.

As raw materials for the production of platinum thin films, etc., by a vapor deposition method, those composed of a large number of organoplatinum compounds have been conventionally known. As such organoplatinum compounds, for example, the following (cyclopentadienyl)trimethyl platinum (IV) complex (Patent Document 1), (1,5-hexadiene)dimethyl platinum (II) (Patent Document 2), and the like have been proposed.

[Chemical Formula 1]

[Chemical Formula 2]

Here, as the required performance of a raw material for vapor deposition, generally, it is required that the material has a high vapor pressure and excellent vaporization properties, and also that the material is capable of film formation at a low temperature and yet has moderate thermal stability. The two kinds of organoplatinum compounds described above do not have this required performance in a well-balanced manner. That is, the (cyclopentadienyl)trimethyl platinum (IV) of Patent Document 1 has excellent vaporization properties, but has a high decomposition temperature, leading to thermal stability that is too high, and thus is unsuitable for low-temperature film formation. Meanwhile, the (1,5-hexadiene)dimethyl platinum (II) of Patent Document 2 has a reduced decomposition temperature and can respond to low-temperature film formation. However, in some rare cases, it happens that the compound decomposes during storage or at the vaporization stage before film formation, for example.

Thus, for the above conventional art, as a platinum raw material for vapor deposition which enables film formation at a low temperature but has suitable thermal stability, and is unlikely to undergo thermal decomposition at the vaporization stage or the like, the applicant for this application has proposed a raw material including the following organoplatinum compound, in which an alkene-amine ligand and an alkyl ligand are coordinated to platinum (Patent Document 3).

[Chemical Formula 3]

(In the formula, n is 1 or more and 5 or less, $R_1$ to $R_5$ are each any one of a hydrogen atom, an alkyl group, an alkenyl group, an alkynyl group, an amino group, an imino group, a cyano group, and an isocyano group, each having 4 or less carbon atoms, and $R_6$ and $R_7$ are each an alkyl group having 1 or more and 3 or less carbon atoms.)

RELATED ART DOCUMENT

Patent Documents

Patent Document 1: JPH 11-292889 A
Patent Document 2: WO 2012/144455 A1
Patent Document 3: JP 2016-211048 A

SUMMARY OF THE INVENTION

Problems to be Solved by the Invention

The raw material including an organoplatinum compound disclosed by the applicant for this application as described above allows for low-temperature film formation and yet has improved thermal stability, and the decomposition of the organoplatinum compound during storage, at the vaporization stage, and the like is also suppressed. Therefore, this raw material including an organoplatinum compound has been capable of effectively responding to the required properties of platinum thin films, etc., and also to the film formation environment/film formation conditions in the past.

However, in recent years, for improving the production efficiency of semiconductor devices and the like, the film formation conditions/film formation environment are becoming more severe, and it is difficult to cope with producing semiconductor devices and the like with the raw material including an organoplatinum compound described above. Specifically, in a thin film production device, a wider film formation area and higher throughput have been demanded. Under such conditions, in the conventional raw material described above, sudden decomposition of the organoplatinum compound or defective film formation due to the lack of film thickness, for example, may occur.

The present invention has been accomplished against the above background, and an object thereof is to find an organoplatinum compound that exerts improved properties over conventional art in terms of the required properties of a raw material for vapor deposition, that is, the balance between vaporization properties and thermal stability, and is capable of responding to low-temperature film formation. Then, the present invention provides an optimal raw material for vapor deposition that applies the organoplatinum compound.

Means for Solving the Problems

With regard to the above problems, if the decomposition of an organoplatinum compound and defective film formation are caused by a wider film formation area, higher throughput, and the like, then it is likely that the thermal stability of the organoplatinum compound applied is insufficient for such film formation conditions. Thus, the present inventors have conducted extensive research to appropriately improve thermal stability while considering the configuration of a conventional organoplatinum compound, and find an organoplatinum compound having an excellent balance between low-temperature film formability and vaporization properties. Then, as a suitable organoplatinum compound, they have found a compound in which a cyclopentene-amine ligand and two alkyl ligands are coordinated to divalent platinum, and arrived at the present invention.

That is, the present invention is drawn to a raw material for vapor deposition for producing a platinum thin film or a platinum compound thin film by a vapor deposition method, the raw material for vapor deposition including an organoplatinum compound represented by the following formula, in which a cyclopentene-amine ligand and an alkyl ligand are coordinated to divalent platinum.

[Chemical Formula 4]

(In the formula, $R_1$, $R_2$, and $R_3$ are each any one of a hydrogen atom, an alkyl group, an alkenyl group, an alkynyl group, an amino group, an imino group, a cyano group, and an isocyano group, each having 4 or less carbon atoms, and $R_4$ and $R_5$ are each an alkyl group having 1 or more and 3 or less carbon atoms.)

Hereinafter, an organoplatinum compound that constitutes the raw material for vapor deposition according to the present invention will be described in detail. As described above, the organoplatinum compound used in the present invention applies a cyclopentene-amine ligand and an alkyl ligand as ligands to platinum. In this organoplatinum compound, the linear alkene ligand in the alkene-amine ligand of the conventional organoplatinum compound described above (Patent Document 3) is replaced with a cyclic alkene ligand (cyclopentene ligand) to thereby achieve the optimization of thermal stability.

The cyclopentene-amine ligand applied in the present invention is, as with the alkene-amine ligand applied in the organoplatinum compound described in Patent Document 3, a ligand having one amine and one double bond. That is, also in the present invention, it is premised that the number of double bonds (C=C bond) in the ligand is made appropriate. As a result, the balance of thermal stability, vaporization properties, and the like is made suitable. When the number of double bonds in a ligand decreases, the thermal stability of the compound improves. However in the present invention, as in Patent Document 3, a ligand in which one amine is bonded, and the number of double bonds is 1, is applied. This is because it is considered that when a ligand having no double bond, such as a diamine ligand is applied, the thermal stability of the compound becomes excessively high, and also the vaporization properties tend to deteriorate.

Then, the present invention applies, as the configuration of the ligand, a ligand composed of cyclopentene, which is a cyclic alkene ligand, and an amine (cyclopentene-amine ligand). According to the present inventors, when a linear alkene ligand is replaced with a cyclic alkene ligand, the thermal stability of the entire platinum compound can be moderately improved. Then, in this case, no deterioration occurs in low-temperature film formability or vaporization properties. As a result, the organoplatinum compound according to the present invention can exert optimal properties in terms of low-temperature film formability, vaporization properties, and thermal stability in total. Accordingly, in the formation of a platinum film or the like over a wide area unexpected decomposition of the organoplatinum compound is not caused, and stable thin film production can be achieved.

Further, in the organoplatinum compound of the present invention, together with the cyclopentene-amine ligand, alkyl ligands ($R_4$, $R_5$) are coordinated to platinum. An alkyl ligand is a hydrocarbon group having a simple configuration, and is a ligand useful in adjusting the molecular weight of a platinum compound. Then, after the decomposition of a platinum compound, an alkyl ligand is released as a low-boiling-point hydrocarbon, and thus is unlikely to form residual impurities. For such advantages, the alkyl ligand is an indispensable ligand together with the cyclopentene-amine ligand.

Here, in the organoplatinum compound applied in the present invention, the cyclopentene-amine ligand or a derivative thereof may have substituents within a predetermined range ($R_1$, $R_2$, $R_3$).

The substituents $R_1$ and $R_2$ on the nitrogen moiety of the cyclopentene-amine ligand are each any one of a hydrogen atom, an alkyl group, an alkenyl group, an alkynyl group, an amino group, an imino group, a cyano group, and an isocyano group, each having 4 or less carbon atoms. The substituents $R_1$ and $R_2$ are each preferably any one of a hydrogen atom, a methyl group, an ethyl group, and a propyl group, and particularly preferably hydrogen, a methyl group, or an ethyl group. When an alkyl group having 3 or more carbon atoms is applied, the alkyl group may be any of linear (n-) and branched (tert-, iso-, sec-), which are structural isomers, but is preferably linear.

The substituent $R_3$ on cyclopentene of the cyclopentene-amine ligand is also any one of a hydrogen atom, an alkyl group, an alkenyl group, an alkynyl group, an amino group, an imino group, a cyano group, and an isocyano group, each having 4 or less carbon atoms. The substituent $R_3$ is preferably a hydrogen atom, a methyl group, or an ethyl group, and particularly preferably a hydrogen atom. When an alkyl group having 3 or more carbon atoms is applied, the alkyl group may be any of linear (n-) and branched (tert-, iso-, sec-), which are structural isomers, but is preferably linear.

In addition, the alkyl ligands $R_4$ and $R_5$, which are the other ligands, are each an alkyl group having 1 or more and 3 or less carbon atoms, that is, any one of a methyl group, an ethyl group, and a propyl group (n-, iso-). $R_4$ and $R_5$ may be the same or different alkyl groups. With an increase in the number of carbon atoms in an alkyl group, the stability of the entire platinum compound tends to decrease. Thus, the number of carbon atoms in each alkyl ligand is specified to be 3 or less. It is preferable that $R_4$ and $R_5$ are both methyl groups. This is because a methyl group becomes low-boiling-point methane after complex decomposition, and thus can be released without leaving impurities in the formed thin metal film.

Incidentally, the platinum described above, which is a central metal to which a cyclopentene-amine ligand and two alkyl ligands are coordinated, is divalent platinum. Many of organoplatinum compounds (platinum complexes) are stable when having divalent or tetravalent positively charged platinum as the central metal. According to the present inventors, when the handleability of the compound at each stage of synthesis, purification, and storage is considered, a compound of divalent platinum can exert moderate stability.

With respect the raw material for vapor deposition according to the present invention described above, specific examples of the configuration of the organoplatinum compound that constitutes the raw material will be shown below. However, the present invention is not limited to the specific examples.

[Chemical Formula 5]

-continued

The raw material for vapor deposition of the present invention described above can be produced by using a suitable platinum salt (platinum compound) as a starting material, and allowing a cyclopentene-amine compound to react therewith. As a platinum salt, one that is an organoplatinum compound of divalent platinum having coordinated thereto the desired alkyl ligands ($R_4$, $R_5$) is preferable. For example, (1,5-hexadiene)dimethyl platinum (the above Chemical Formula 2, Patent Document 2) and like organoplatinum compounds are applicable.

Then, the raw material for vapor deposition according to the present invention is useful in the production of a platinum thin film, etc., by a vapor deposition method such as a CVD method or an ALD method. According to this method for forming a thin film, a raw material including an organoplatinum compound is vaporized into a reactant gas, the reactant gas is introduced onto the substrate surface, and the organoplatinum compound is decomposed to deposit platinum, in which the organoplatinum compound according to the present invention described above is used as the raw material.

As the reaction atmosphere at the time of platinum formation, a reducing atmosphere is preferable. The raw material of the present invention tends to show excellent low-temperature film formability particularly in a reducing atmosphere. In addition, use of a reducing atmosphere is also advantageous in that when other thin metal films are formed together with a platinum thin film, the oxidation of the other thin metal films can be suppressed. For example, the application of a platinum thin film to a solid electrode (Ni—Pt silicide electrode) of a FET (field-effect transistor) is known. When a condition for the formation of a platinum thin film is a reducing atmosphere, the oxidation of a Ni thin film can be suppressed. Incidentally, as the reducing atmosphere, it is preferable to introduce hydrogen or ammonia as the reactant gas, and hydrogen is particularly preferable.

The film formation temperature for a platinum thin film, etc., that is, the temperature of heating the organoplatinum compound on the substrate is preferably 100° C. or more and 350° C. or less. This is because when the temperature is less than 100° C., the film formation reaction is difficult to proceed, making it difficult to obtain a necessary thickness, while when the temperature is more than 350° C., impacts on the substrate are concerned. In addition, in consideration of low-temperature film formation, which is the gist of the present invention, a film formation temperature of more than 350° C. is not suitable.

Advantageous Effects of the Invention

As described above, the organoplatinum compound that constitutes the raw material for vapor deposition according to the present invention has a high vapor pressure, allows for the production of a platinum thin film at a low temperature, and also has moderate thermal stability. Incidentally, the raw material according to the present invention is suitable for a vapor deposition method such as a CVD method or an ALD method.

DESCRIPTION OF EMBODIMENTS

Hereinafter, best modes for carrying out the present invention will be described. In this embodiment, three kinds of organoplatinum compounds (Example 1 to Example 3) were synthesized. The physical properties of the synthesized organoplatinum compounds were evaluated, and they were used as raw materials for vapor deposition to perform a film formation test.

[Chemical Formula 6]

Example 1    Example 2    Example 3

Example 1

To a flask containing 90 ml of hexane, 1.62 g (14.6 mmol) of N,N-dimethyl-3-cyclopentene-1-amine and 1.78 g (5.8 mmol) of (1,5-hexadiene)dimethyl platinum were each added in this order and stirred at room temperature for 16 hours. After the completion of the reaction, the mixture was concentrated to give a white solid. The obtained white solid was sublimated and purified to give 1.68 g (5.0 mmol) of (N,N-dimethyl-3-cyclopentene-1-amine)dimethyl platinum, the desired product (yield: 86%). The synthesis reaction formula of the organoplatinum compound of Example 1 is as follows.

[Chemical Formula 7]

Example 2

To a flask containing 50 ml of hexane, 0.27 g (3.3 mmol) of 3-cyclopentene-1-amine and 0.68 g (2.2 mmol) of (1,5-hexadiene)dimethyl platinum were each added in this order and stirred at room temperature for 3 hours. After the completion of the reaction, the mixture was concentrated to give a white solid. The obtained white solid was sublimated and purified to give 0.61 g (2.0 mmol) of (3-cyclopentene-1-amine)dimethyl platinum, the desired product (yield: 91%). The synthesis reaction formula of the organoplatinum compound of Example 2 is as follows.

[Chemical Formula 8]

Example 3

To a flask containing 30 ml of hexane, 0.21 g (2.2 mmol) of N-methyl-3-cyclopentene-1-amine and 0.45 g (1.5 mmol) of (1,5-hexadiene)dimethyl platinum were each added in this order and stirred at room temperature for 15 hours. After the completion of the reaction, the mixture was concentrated to give a white solid. The obtained white solid was sublimated and purified to give 0.43 g (1.3 mmol) of dimethyl (N-methyl-3-cyclopentene-1-amine) platinum, the desired product (yield: 87%). The synthesis reaction formula of the organoplatinum compound of Example 3 is as follows.

[Chemical Formula 9]

Comparative Example

As a comparative example for the above examples, dimethyl(N,N-dimethyl-3-buten-1-amine) platinum, which is an organoplatinum compound described in conventional art (Patent Document 3), was produced.

To a flask containing 50 ml of hexane, 0.75 g (7.5 mmol) of N,N-dimethyl-3-buten-1-amine and 1.54 g (5.0 mmol) of (1,4-hexadiene)dimethyl platinum were each added in this order and stirred at room temperature for 20 hours. After the completion of the reaction, the mixture was concentrated to give a white solid. The obtained white solid was sublimated and purified to give 1.55 g (4.8 mmol) of dimethyl(N,N-dimethyl-3-buten-1-amine) platinum, the desired product (yield: 96%). The synthesis reaction formula of the organoplatinum compound of this comparative example is as follows.

[Chemical Formula 10]

Evaluation of Physical Properties:

The physical properties of the organoplatinum compound produced in Example 1 ((N,N-dimethyl-3-cyclopentene-1-amine)dimethyl platinum) were evaluated by TG-DTA. In the analysis, by use of TG-DTA2000SA manufactured by BRUKER, in a nitrogen atmosphere, the organoplatinum compound sample (5 mg) was heated at a temperature rise rate of 5° C./min to a measurement temperature range, that is, room temperature to 450° C., and changes in the heat quantity and the weight of the sample at that time were observed. The results are shown in FIG. 1.

Figure 1:
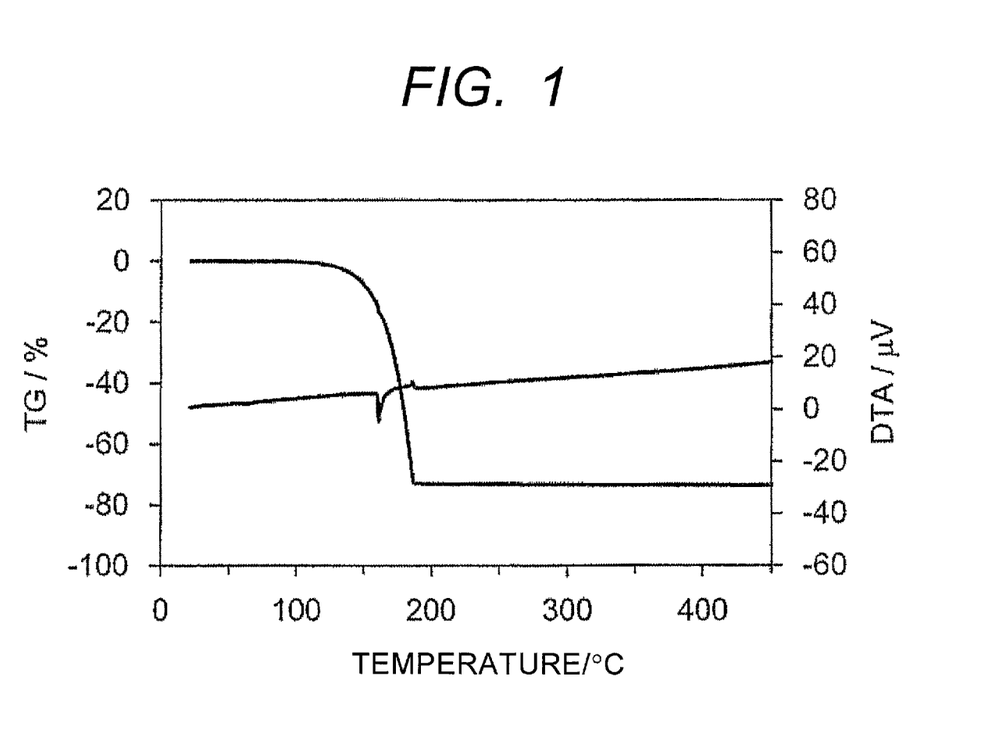
FIG. 1 illustrates A TG-DTA curve of an organoplatinum compound of Example 1.

In FIG. 1, from the results of DTA, the organoplatinum compound of Example 1 has a melting point of about 159° C. from the endothermic peak and a decomposition temperature of about 186° C. from the exothermic peak. Generally, the raw material heating temperature in a vapor deposition method is often set at a temperature around 100° C., and it can be seen that the organoplatinum compound of Example 1 has sufficient thermal stability at such a raw material heating temperature. In addition, in order to obtain a higher vapor pressure, it is expected to increase the heating temperature by about 10° C. to 30° C., and it can be said that the organoplatinum compound of Example 1 can respond also to such heating conditions.

In addition, as a result of examining the results of TG, it can be seen that in the organoplatinum compound of Example 1, vaporization is almost completed at the time when the decomposition temperature is reached. It can be seen that this platinum compound is vaporized quickly at a relatively low temperature, and its vaporization properties are also excellent. In addition, the amount of residues resulting from the decomposition of the compound is relatively large. It is estimated that this residue is metal platinum. These TG-DTA results show that the platinum compound of Example 1 can be vaporized at a relatively low temperature, and decomposition occurs quickly with vaporization, and also show that the compound is suitable for low-temperature film formation.

Then, the organoplatinum compounds of Example 2, Example 3, and the comparative example were also analyzed in the same manner. The results of TG-DTA of each example are shown in Table 1.

TABLE 1

| Organoplatinum compound | | Melting point | Decomposition temperature |
|---|---|---|---|
| Example 1 | | 159° C. | 186° C. |
| Example 2 | | 128° C. | 169° C. |
| Example 3 | | 99° C. | 184° C. |
| Comparative Example | | 75° C. | 150° C. |

As to the organoplatinum compounds of Examples 2 and 3, as compared with the compound of Example 1, although a decrease in the melting point was seen, the decomposition temperature was equal or only slightly lower. Therefore, it was shown that the organoplatinum compounds of the examples all have suitable vaporization properties and thermal stability. It can be seen that the melting point and the decomposition temperature of the organoplatinum compound of the comparative example are lower as compared with each example. Therefore, it was confirmed that the platinum compound of each example has higher thermal stability over conventional art.

Evaluation of Thermal Stability by Heating Test:

The above TG-DTA is an analysis method excellent in that physical properties intrinsic to a compound (decomposition temperature) can be measured statically and accurately. However, in the raw material heating operation at the time of actual thin film production, even when the heating temperature is lower than the decomposition temperature, due to prolonged heating, local decomposition may occur in the organic compound. In addition, chained decomposition may occur from such local decomposition as a starting point. Thus, it was decided to perform dynamic thermal stability evaluation given a raw material heating operation in thin film production. In this evaluation test, the organoplatinum compounds of Example 1 and the comparative example were heated for a predetermined period of time, and whether compound decomposition occurred was judged. As a specific method, 0.2 g of each of the organoplatinum compounds of Example 1 and the comparative example was collected and placed in a test tube, and heated in air at 100° C. for 1 hour. Then, after the 1-hour heating, whether there were changes in the appearance of the platinum compound was checked.

In this heating test, in the organoplatinum compound of Example 1, no change was seen in the appearance before and after heating, and the white solid state was maintained. Meanwhile, the organoplatinum compound of the comparative example had turned into a black solid after heating for 1 hour. This is regarded as an indication of decomposition (partial decomposition) of the organoplatinum compound. For both of the organoplatinum compounds, the heating temperature (100° C.) in this heating test is lower than the decomposition temperature. In Example 1, decomposition of the compound was not seen at all, but decomposition occurred in the comparative example. This shows that the organoplatinum compound of the comparative example may decompose due to prolonged heating even at a temperature lower than the decomposition temperature, that is, its thermal stability is poor.

In order to respond to the film formation conditions including wide-area film formation, high-throughput film formation, and the like, which is an object of the invention, an organoplatinum compound raw material having a high vapor pressure is required. This means the application of an organoplatinum compound having so high a thermal stability that it can be heated to a temperature at which the desired vapor pressure is shown. From the results of the above heating test, it was confirmed that the organoplatinum compound of the example has higher thermal stability as compared with the comparative example. That is, it can be said that the organoplatinum compound of the example has a better balance between thermal stability and vaporization properties as compared with the comparative example. Then, the organoplatinum compound of the example can suitably respond also to wide-area film formation and high-throughput film formation.

Film Formation Test:

Next, a film formation test was performed, in which a platinum thin film was formed by a CVD method by use of the organoplatinum compound produced in Example 1 ((N,N-dimethyl-3-cyclopentene-1-amine)dimethyl platinum) as a raw material compound. In this film formation test, a hot-wall type thermal CVD device was used as a film formation device. As the reactant gas, hydrogen was passed at a constant flow rate with a mass flow controller. The film formation conditions are as follows.

Substrate: $SiO_2$ and Si
Substrate dimension: 15 mm×15 mm
Film formation temperature: 175° C.
Specimen temperature: 100° C.
Film formation pressure: 5 torr
Reactant gas (hydrogen) flow rate: 100 sccm
Film formation time: 120 min As a result of the film formation test, it was confirmed that a platinum thin film can be formed on any of the substrates ($SiO_2$, Si). As a result of measuring the film thickness and the specific resistance, the Pt film thickness on the $SiO_2$ substrate was 18 nm, while the Pt film thickness on the Si substrate was 13 nm, that is, the platinum thin film was formed to a sufficient film thickness in each case. In addition, as a result of measuring the specific resistance of each thin film, the values were as excellent as 36 $\mu\Omega\cdot cm$ and 40 $\mu\Omega\cdot cm$, respectively.

Figure 2:
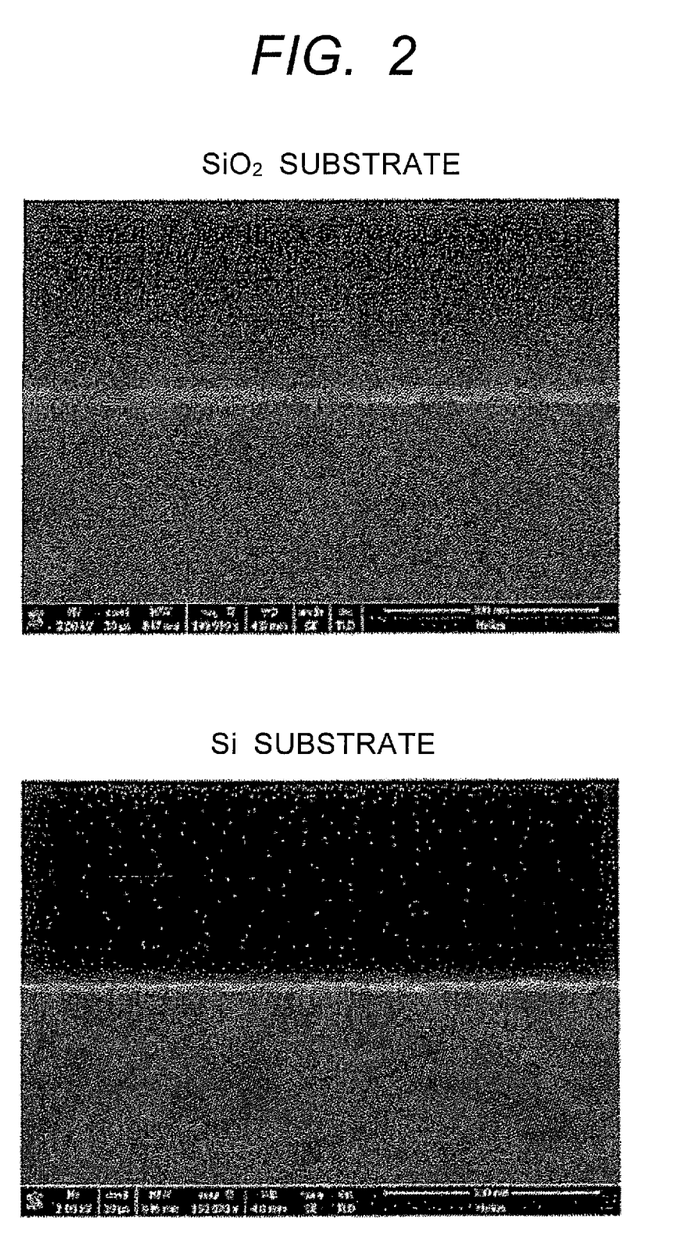
FIG. 2 shows SEM photographs of cross-sections of platinum thin films produced from the organoplatinum compound of Example 1 as a raw material.

FIG. 2 shows SEM photographs of cross-sections of the platinum thin films formed in this embodiment. The thin films formed in this embodiment all had a uniform film thickness, and the surface smoothness was also excellent. From the results of this film formation test, it was confirmed that the organoplatinum compound of the example has suitable vaporization properties and thermal stability as a raw material compound for vapor deposition, and is useful in low-temperature film formation.

INDUSTRIAL APPLICABILITY

The raw material for vapor deposition according to the present invention has a high vapor pressure and is capable of forming a high-precision platinum thin film, etc., at a low temperature, and also has moderate thermal stability and excellent handleability. The present invention is useful in the formation of electrode/wiring materials for various semiconductor elements and semiconductor devices. In particular, the present invention is also effective in film formation on a solid structure, and also applicable to the formation of a solid electrode of a field effect transistor (solid Ni—Pt silicide electrode), which has a three-dimensional structure, for example.

The invention claimed is:

1. A raw material for vapor deposition for producing a platinum thin film or a platinum compound thin film by a vapor deposition method, the raw material for vapor deposition comprising
   an organoplatinum compound represented by a following formula, in which a cyclopentene-amine ligand and an alkyl ligand are coordinated to divalent platinum:

[Chemical Formula 1]

(wherein $R_1$, $R_2$, and $R_3$ are each any one of a hydrogen atom, an alkyl group, an alkenyl group, an alkynyl group, an amino group, an imino group, a cyano group, and an isocyano group, each having 4 or less carbon atoms, and
   $R_4$ and $R_5$ are each an alkyl group having 1 or more and 3 or less carbon atoms).

2. The raw material for vapor deposition according to claim 1, wherein $R_1$ and $R_2$ are each any one of hydrogen, a methyl group, and an ethyl group.

3. The raw material for vapor deposition according to claim 1, wherein $R_3$ is hydrogen.

4. The raw material for vapor deposition according to claim 1, wherein $R_4$ and $R_5$ are both methyl groups.

5. A vapor deposition method for a platinum thin film or a platinum compound thin film, comprising:
   vaporizing a raw material including an organoplatinum compound into a raw material gas; and heating the raw material gas while introducing the raw material gas onto a substrate surface,
   wherein the raw material for vapor deposition defined in claim 1 is used as the raw material.

6. The raw material for vapor deposition according to claim 2, wherein $R_3$ is hydrogen.

7. The raw material for vapor deposition according to claim 2, wherein $R_4$ and $R_5$ are both methyl groups.

8. The raw material for vapor deposition according to claim 3, wherein $R_4$ and $R_5$ are both methyl groups.

9. A vapor deposition method for a platinum thin film or a platinum compound thin film, comprising:
   vaporizing a raw material including an organoplatinum compound into a raw material gas; and heating the raw material gas while introducing the raw material gas onto a substrate surface,
   wherein the raw material for vapor deposition defined in claim 2 is used as the raw material.

10. A vapor deposition method for a platinum thin film or a platinum compound thin film, comprising:
    vaporizing a raw material including an organoplatinum compound into a raw material gas; and heating the raw material gas while introducing the raw material gas onto a substrate surface,
    wherein the raw material for vapor deposition defined in claim 3 is used as the raw material.

11. A vapor deposition method for a platinum thin film or a platinum compound thin film, comprising:
vaporizing a raw material including an organoplatinum compound into a raw material gas; and heating the raw material gas while introducing the raw material gas onto a substrate surface,
wherein the raw material for vapor deposition defined in claim 4 is used as the raw material.

* * * * *